United States Patent [19]

Harich et al.

[11] Patent Number: 5,631,001
[45] Date of Patent: *May 20, 1997

[54] ANTIMICROBIAL GRAPEFRUIT EXTRACT

[76] Inventors: Jakob Harich, Winter Springs, Fla.;
Elizabeth K. Harich, administratrix,
106 Concord Dr. - P.O. Box 181279,
Casselberry, Fla. 32718

[ * ] Notice: The term of this patent shall not extend beyond the expiration date of Pat. No. 5,425,944.

[21] Appl. No.: 470,225

[22] Filed: Jun. 6, 1995

Related U.S. Application Data

[62] Division of Ser. No. 967,158, Oct. 27, 1992, Pat. No. 5,425,944.

[51] Int. Cl.$^6$ ............................ A61K 7/26; A61K 35/78
[52] U.S. Cl. .................... 424/58; 424/195.1; 514/464; 514/474; 514/885; 514/934
[58] Field of Search ...................... 424/195.1, 58; 514/934, 885, 464, 474

[56] References Cited

U.S. PATENT DOCUMENTS 4,021,548  5/1977  Harich et al. .................... 424/195.1
4,420,471  12/1983  Elton et al. ...................... 424/49
4,983,637  1/1991  Herman ........................... 514/724
5,425,944  6/1995  Harich ............................. 424/195.1

OTHER PUBLICATIONS

Pauling & Cameron; *Statement on the Treatment of Aids*; 1987.
Linus Pauling Institute Newsletter: *LPI Scientists Find Vitamin C Inhibits Aids Virus in Cell Culture*; Winter 1990 pp. 1&4.
Linus Pauling Institute Newsletter: *Abrupt Termination of High Daily Intake of Vitamin C*; vol. 2, No. 7–one page.
Harakeh & Jariwalla: *Comparative Study of Anti HIV Activities*; Am J Clin Nutr 1991:54 pp. 12315–12355.
Harakeh, Jariwalla & Pauling: *Suppression of Human Immunodeficiency Virus Replication*; Proc. Natl. Acad. Sci. USA; Sep. 90:87–pp. 7245–7249.

Primary Examiner—John W. Rollins

[57] ABSTRACT

A ground mixture (80:20 by weight) of dried grapefruit seeds and grapefruit pulp respectively is subjected to extraction using an equal amount by weight of glycerin. The resulting extract is an effective bactericide, fungicide, and virucide, and is expected to be particularly effective in the treatment of HIV infections.

8 Claims, No Drawings

ANTIMICROBIAL GRAPEFRUIT EXTRACT

This application is a division, of application Ser. No. 07/967,158, filed Oct. 27, 1992, now U.S. Pat. No. 5,425,944.

BACKGROUND AND SUMMARY OF THE INVENTION

The present invention is directed to an improved, multipurpose disinfectant and, more particularly, to an extract of ground grapefruit seeds and pulp which is particularly useful as a bactericide, fungicide, virucide, and is believed to be particularly effective in the treatment of HIV infections.

Ascorbic acid (Vitamin C) is known to be a disinfectant which can be effective to kill various pathogenic microorganisms. There is some evidence that ascorbic acid may even be used to inhibit the activity and growth of the AIDS virus (HIV).

Recent studies indicate that ascorbic acid (Vitamin C) may be effective to inactivate certain viruses including the polio virus, Herpes virus, vaccinia virus and hepatitis virus. Also, the intracellular replication of rhino virus, Rous Sarcoma virus and human T cell leukemia virus have been shown to be suppressed by ascorbic acid. Some patients with poliomyelitis, hepatitis, and infectious mononucleosis have improved with a Vitamin C treatment. There is also some evidence that large doses of synthesized ascorbic acid (10-20 grams/day) may inhibit the activity and growth of HIV.

Ascorbic acid is found in many plants, particularly citrus fruits. For example, U.S. Pat. No. 4,021,548 teaches that grapefruit pulp from which a product, probably having an ascorbic acid content, can be extracted having antifungal and antibacterial properties. In U.S. Pat. No. 4,468,372, there is disclosed the use of a grapefruit seed extract, again probably containing ascorbic acid, impregnated into silicate pellets used to destroy air-borne bacteria, fungi and viruses in an airstream passing thereover.

In the present invention, however, it has been found that a certain extract produced from the reaction of a prescribed amount of glycerin with a substantially equal amount by weight of a ground mixture of 80:20 by weight of dried grapefruit seeds and pulp respectively results in a superior disinfectant that may be used as a bactericide, fungicide, and virucide, and even appears to be effective in the treatment of HIV infections. There appear to be two advantages to the extract according to the present invention. First of all, as the extract is formed of both seeds and pulp, the reaction product contains a significant quantity (14-15% by weight) of bioflavonoids along with ascorbic acid (approximately 16.5% by weight). Secondly, as the ascorbic acid is produced naturally, rather than by synthesis, it is significantly more stable. A common problem with synthetically formed ascorbic acid is that it has a shelf-life of only approximately 6-8 weeks. The resulting natural extract may be used either as a liquid, or it may be dehydrated, stored, and used in dry form.

In its broadest aspect, the present invention is directed to a certain grapefruit extract obtained from reacting a ground mixture of 80:20 dried grapefruit seeds:grapefruit pulp by weight with approxiamtely an equal weight of a glycerin solution and the extraction technique therefor. The resulting extract is useful as an effective disinfectant for use against such microorganisms as bacteria, fungi, and viruses (even HIV). The active constituents of the extract are a combination of natural ascorbic acid and bioflavonoids. The extraction process is carried out using approximately equal amounts of glycerin and the seed/pulp mixture at a temperature of approximately 150° C.

More particularly, the process according to the present invention includes the step of separating the seed and pulp of certain types of tree-ripened grapefruit from the remainder of the fruit and drying the seed and pulp for 24-48 hours at a temperature in the range of 150°-200° C. The seed and pulp are then tested for pesticides and only non-contaminated seed and pulp are selected for processing. The dried, non-contaminated seed and pulp is mixed at a ratio of 80:20 seed/pulp by weight. The mixture is then ground in a hammermill to small particles, whereupon the ground mixture is placed inside some type of mesh bag or perforated container which is then placed in a reaction vessel. Previously, a glycerin solution in an amount by weight approximately equal to the weight of the ground mixture has been placed in the vessel and heated to a temperature of at least approximately 150° C. The vessel is sealed and the glycerin solution is then circulated through the extraction chamber and past an external ultraviolet system and magnetic system which helps to stabilize the ingredients and to remove ferrous metallic particles therefrom. The glycerin circulation is continued at the same temperature for approximately 3-4 hours, whereupon the temperature is reduced to approximately 60° C. while the pressure within the chamber is increased to a range of 2,500-3,000 lbs/sq. inch. There results a syrup and a residue in the reaction chamber. The syrup is then passed through a force filter system having a 300-350 mesh nylon filter to obtain a heavy viscous lemon yellow liquid having a pH in the range of 2.5-3.0. This is the reaction product that is either then diluted and used in various applications or else dehydrated and used in various applications.

It is therefore an object of the present invention to provide a new disinfectant composition as the extraction product of grapefruit seeds and pulp.

It is a further object of this invention to provide an improved grapefruit extract which is effective as a disinfectant for various microorganisms.

It is yet another object of the present invention to provide an improved technique for extracting a disinfecting composition as the reaction product from the seeds and pulp of grapefruit.

Another object of the present invention is to provide an improved bactericide, fungicide and virucide.

Another object of the present invention is to provide a new treatment for treating HIV infections.

Another object of the present invention is to provide an effective treatment for salmonella and escherichia in fish and poultry.

Additional objects and advantages of the invention will become apparent from reading the following detailed description in conjunction with the examples given. The invention consists of the novel steps, methods, processes, procedures, compositions, products described.

In accordance with the present invention, the starting material for the reactive product is grapefruit seeds and pulp. The grapefruit selected is tree-ripened in a climate with cool days and nights which better establishes the trace elements and oils. While the grapefruit may be grown in a variety of locations, the climate must be suitable to provide substantial amounts of the active ingredients, so that the reactive products will be effective. Locations known to have such a climate include Africa, Florida, and Peru. Also, the grapefruit must be grown in an environment in which substantially few, if any, chemical pesticides are used. As will be seen hereinafter, seeds and pulp contaminated with pesticides must be disposed of and cannot be used. The following types of grapefruit have been determined to provide useful raw material: Albedo, Ducan, March, Thompson, Ruby Red and Shaddon.

The pulp is located immediately under the hard outer rind of the skin of a fresh grapefruit and is obtained by mechanically shaving the rind portion from the skin, after the juice and section skins have been previously removed. The separation of the rind from the inner pulp layer of the skin should be accomplished in such a manner that the inner pulp is not damaged.

The seed and pulp are then dried immediately through a drying process to remove moisture and water percentage. Exposure of the seed and pulp to a temperature in the range of 150°–200° C. for 24–48 hours develops a deep brown color and a good starting product.

The dry seeds are mixed in a weight ratio of 80% seed:20% pulp. The dried seed and pulp are ground in a hammermill into small particles and either proceed to testing or storage. Immediately prior to extraction, the ground mixture of seed and pulp, whether processed directly from the hammermill or from storage, is subjected to a test for pesticides. This test is accomplished according to conventional testing techniques on a Perkin-Elmer Atomic Absorbsion Unit provided with hollow cathode lamps, During the testing, seed and/or pulp contaminated with pesticide is removed.

In accordance with the present invention, the seed/pulp mixture is then reacted with glycerin at an elevated temperature. The reaction product is subjected to the influence of ultraviolet radiation and a magnetic treatment, which produces a stable reaction product free of ferromagnetic particles. Preferably, the glycerin extraction solution is provided in the reaction vessel in a weight quantity approximately equal to the weight of the ground mixture to be reacted. The glycerin is preferably U.S.P. grade 99.7%.

The following specific examples are presented to afford a better understanding of the present invention to those skilled in the art. It is to be understood that these examples are intended to be illustrative only and are not intended to limit the invention in any way.

EXAMPLE 1

Two lbs. (908 grams) of glycerin U.S.P. 99.7% is placed in a stainless steel cylinder which includes an inlet and an outlet tube therein. In the center there is a stainless steel shaft which moves up and down and includes a stirring rod. When the glycerin reaches its elevated temperature of 150° C., two lbs. (908 grams) of the ground seed/pulp mixture is placed in a stainless wire mesh sack and suspended in the stainless steel cylinder, which is then close and sealed. The reaction vessel includes a ½" bottom outlet and a ½" top inlet. The outlet system is connected to a stainless steel pump which transfers the liquid through an ultraviolet treatment stage and a magnetic treatment stage. The ultraviolet system consists of two circular 5" tubes. The conduit carrying the recirculated liquid passes through the center of the two tubes. The ultraviolet tubes short spectrum is 254 manometers, 2537Å, and the long spectrum is 365 manometers, 3650Å. The magnetic gauss strength is 350.

The reaction process begins by circulating the glycerin through the system at a temperature of 150° C. for 3–4 hours. The temperature is then reduced to 60° C. and the pressure within the tank is increased from atmospheric to 2,500–3,000 lbs. of hydraulic force. This pressure forces the trace elements from the seed and pulp into the extraction liquid. After the extraction is completed, the liquid is cooled and a residue remains. The residue may be used and mixed into fertilizer for gardening application. The extracted liquid appears to be a deep brown syrup. the liquid is then filtered through a force filter system of 300–350 mesh nylon to achieve the final extract. The extract has the following properties:

| Appearance | Liquid/Heavy Viscous |
|---|---|
| Color (Gardner) | 2, lemon yellow |
| Specific gravity (25° C.) | 1.110 |
| Density (lbs./gal.) | 9.37 |
| pH (25° F.) | 2.5–3.0 |
| Flash point (°F.) | 292 |
| Viscosity index | −23.2 |
| Surface tension, Avg. of 5 readings (dynes/cm) | 40.0 |
| Apparent interfacial tension (dynes/cm) | 5.0 |
| True corrected interfacial tension (dynes/cm) | 4.5 |

EXAMPLE 2

An analysis of the extract produced in accordance with Example 1 shows the following ingredients in the indicated amount:

| Ingredient | Percentage |
|---|---|
| Active | |
| Vitamin C (Ascorbic acid) | 16.5 |
| Crude protein | 2.0 |
| Crude fat | 1.0 |
| Nitrogen-free extract (includes Bioflavonoids 14–15%) | 39.6 |
| Inert | |
| Glycerin | 30.0 |
| Mineral ash (max) | 0.5 |
| Crude fiber (max) | 0.4 |
| Moisture (max) | 10.0 |

EXAMPLE 3

The disinfectant of Example 1 was used in an efficacy test to determine the effect of the extract on various bacteria, yeast and fungi, including *staphylococcus aureus, streptococcus faecilis, bacillus SPP, escherichia coli (E coli), salmonella SPP, shigella SPP, pseudomonas aeruginosa, candida albicans,* and *aspergillus nigers.* The bacteria and yeast were all those isolated from clinical specimens, while *aspergillus niger* strains were isolated from natural sources.

The bacteria were each cultured in tryptic soy broth (TSB) at 37° C. for 18 hours. The yeast and other fungi were each cultured on Sabouraud Dextrose Agar (SDA) at room temperature for 48 hours and 7 days, respectively. On the day of the experiment, the cultures of yeast and fungi were washed with 5 ml of Sabouraud dextrose broth (SDB).

In a first test, three kinds of utensils were applied. These included stainless cylinder cups, glass rods, and cotton swabs. The utensils were immersed in microbial cultures and then separately put into the extract solution at dilutions of 1:100, 1:1000, 1:2000, 1:5000, and 1:10,000. At the end of 5 and 15 minutes, and at the end of 1, 2 and 24 hours, and one time later, the utensils were observed for growth or no growth. The results are tabulated in Table 1 below.

to provide a pH of 3, 5, 7, 9 and 11, respectively. These treated preparations were diluted with water of the following ratios: 1:100, 1:1000 and 1:10,000. The experiment was carried out on the contaminated cups. The further procedure

TABLE 1

Table 1 Efficacy of DF-100 (liquid) as a disinfectant on stainless cylinder cups, glass rods and cotton swabs contaminated microorganisms (40 isolates tested)

| | Stainless cups | | | | | | Glass rods | | | | | | Cotton swabs | | | | | |
|---|---|---|---|---|---|---|---|---|---|---|---|---|---|---|---|---|---|---|
| | Cumulative No. (%) of microorganisms being killed at* | | | | | | | | | | | | | | | | | |
| Dilution | 5 m | 15 m | 1 h | 2 h | 24 h> | 24 h | 5 m | 15 m | 1 h | 2 h | 24 h> | 24 h | 5 m | 15 m | 1 h | 2 h | 24 h> | 24 h |
| 1:100 | 85.0 | 95.0 | 100 | 100 | 100 | 100 | 85.0 | 97.5 | 100 | 100 | 100 | 100 | 82.5 | 92.5 | 95.0 | 100 | 100 | 100 |
| 1:1,000 | 60.0 | 77.5 | 87.5 | 90.0 | 100 | 100 | 65.0 | 82.5 | 92.5 | 92.5 | 100 | 100 | 55.0 | 70.0 | 77.5 | 85.0 | 100 | 100 |
| 1:2,000 | 57.5 | 67.5 | 77.5 | 85.0 | 95.0 | 100 | 57.5 | 70.0 | 77.5 | 85.0 | 95.0 | 100 | 37.5 | 52.5 | 70.0 | 77.5 | 90.0 | 100 |
| 1:5,000 | 47.5 | 65.0 | 70.0 | 80.0 | 95.0 | 100 | 50.0 | 65.0 | 72.5 | 80.0 | 95.0 | 100 | 22.5 | 40.0 | 62.5 | 77.5 | 82.5 | 100 |
| 1:10,000 | 40.0 | 47.5 | 62.5 | 90.0 | 90.0 | 100 | 40.0 | 47.5 | 62.5 | 70.0 | 90.0 | 100 | 7.5 | 15.0 | 32.5 | 57.5 | 80.0 | 100 |

*The results were observed as growth and no growth in broth and on agar media

The effect of organic matter on the efficacy of the extract was also done by using blood as the representative. The experiment was carried out on the contaminated stainless cylinder cups. For each growth culture, it was divided into two parts. One part was added with 5% human blood, while another part remained untreated. Afterwards, the test was conducted as described above. The results of this test are set forth in Table 2.

was done as described previously. For control, water was also treated with 0.1N NCl and 0.1N NaOH to give the same pH as above, after which treated water was diluted with water in a ratio of 1:100. The results are tabulated in Table 3.

TABLE 2

Table 2 Efficacy of dF-100 (liquid) as a disinfectant on stainless cylinder cups contaminated with microornisms in the absence and presence of blood (20 isolates tested)

| | Absence of blood | | | | | | Presence of blood | | | | | |
|---|---|---|---|---|---|---|---|---|---|---|---|---|
| | Cumulative nO. (%) of microorganisms being killed at* | | | | | | | | | | | |
| Dilution | 5 m | 15 m | 1 h | 2 h | 24 h> | 24 h | 5 m | 15 m | 1 h | 2 h | 24 h> | 24 h |
| 1:100 | 80.0 | 90.0 | 100 | 100 | 100 | 100 | 80.0 | 90.0 | 100 | 100 | 100 | 100 |
| 1:1,000 | 65.0 | 80.0 | 95.0 | 95.0 | 100 | 100 | 65.0 | 75.0 | 90.0 | 90.0 | 100 | 100 |
| 1:2,000 | 60.0 | 65.0 | 85.0 | 90.0 | 100 | 100 | 65.0 | 65.0 | 85.0 | 90.0 | 100 | 100 |
| 1:5,000 | 50.0 | 60.0 | 80.0 | 90.0 | 95.0 | 100 | 50.0 | 65.0 | 75.0 | 90.0 | 100 | 100 |
| 1:10,000 | 45.0 | 45.0 | 60.0 | 85.0 | 95.0 | 100 | 45.0 | 45.0 | 65.0 | 80.0 | 95.0 | 100 |

*The results were observed as growth and no growth in broth and on agar media

The effects of pH on the efficacy of the extract was then tested by treating the extract with 0.1N HCl and 0.1N NaOH

TABLE 3

Table 3 Efficacy of DF-100 (liquid) treated at different pH as a disinfectant on stainless cylinder cups contaminated with microorganisms (16 isolates tested)

| | 1:100 | | | | | | 1:1,000 | | | | | | 1:10,000 | | | | | |
|---|---|---|---|---|---|---|---|---|---|---|---|---|---|---|---|---|---|---|
| | Cumulative No. (%) of microorganisms being killed at* | | | | | | | | | | | | | | | | | |
| pH | 5 m | 15 m | 1 h | 2 h | 24 h> | 24 h | 5 m | 15 m | 1 h | 2 h | 24 h> | 24 h | 5 m | 15 m | 1 h | 2 h | 24 h> | 24 h |
| 3 | 93.8 | 93.8 | 100 | 100 | 100 | 100 | 56.3 | 81.3 | 87.5 | 100 | 100 | 100 | 31.3 | 50.0 | 62.5 | 75.0 | 81.3 | 100 |
| 5 | 87.5 | 100 | 100 | 100 | 100 | 100 | 56.3 | 75.0 | 87.5 | 100 | 100 | 100 | 43.8 | 62.5 | 75.0 | 75.0 | 81.3 | 100 |
| 7 | 93.8 | 100 | 100 | 100 | 100 | 100 | 56.3 | 75.0 | 93.8 | 100 | 100 | 100 | 18.8 | 31.3 | 31.3 | 31.3 | 56.3 | 100 |
| 9 | 87.5 | 93.8 | 100 | 100 | 100 | 100 | 56.3 | 75.0 | 87.5 | 93.8 | 100 | 100 | 18.8 | 31.3 | 31.3 | 37.5 | 43.8 | 100 |
| 11 | 87.5 | 93.8 | 100 | 100 | 100 | 100 | 56.3 | 75.0 | 87.5 | 100 | 100 | 100 | 43.8 | 62.5 | 75.0 | 81.3 | 93.8 | 100 |

*The results were observed as growth and no growth in broth and on agar media

The overall results of this example revealed that the extract possesses an antimicrobial activity even though diluted up to 1:10,000, as it shows a disinfective property on either contaminated stainless cups, glass rods or cotton swabs tested. The killing effect of this preparation is better on smooth surface utensils such as the stainless steel cups and glass rods rather than the rough ones, such as cotton swabs. According to the results obtained, the extract shows a very good antimicrobial activity when diluted to 1:100 (100% of the tested microorganisms were killed within 1–2 hours) and a good activity when it is diluted to 1:1000 (100% of tested microorganisms are killed within 24 hours).

When blood cultures were applied to the utensils, the extract showed no different effect from those utensils applied with normal cultures. In the pH testing, it was found that all pH's (pH 3, 5, 7, 9 and 11) tested to demonstrate some antimicrobial activity even up to dilutions of 1:10,000. when the pretreated liquid is diluted to either 1:100 or 1:1000, no significant difference is present as a result of pH differences. However, when the extract is diluted to 1:10,000, a lower disinfective property of the extract with the pH 7 and 9 was noticed.

EXAMPLE 4

The following test is based upon observation of undocumented studies and expected results in the treatment of HIV infections. The extract of Example 1 is diluted to a mouth rinse in the range of 50–100 ppm. Human subjects who have tested positive for HIV are utilized. The HIV infection is noted in the blood and the tonsils are also swollen. Approximately 100 mg. of the diluted extract (50 ppm) is used as a mouth rinse and swallowed twice a day for the first week. The concentration is then increased to 100 ppm and the same amount is used as a mouth rinse and swallowed twice a day up to three months or until the blood is clear and the tonsils stop swelling. Subsequently, the patients repeat a single dosage of the treatment periodically.

Patients so treated are clear of the HIV infection and have remained relatively clear thereof for a period of nine months. It is believed that the same treatment as described hereinabove is effective in the treatment of other viral infections as well.

EXAMPLE 5

As a result of earlier testing of the disinfectant described in applicant's U.S. Pat. No. 4,021,548, the following is believed to be a proper treatment against pathogenic microorganisms. The extract, when used at a dilution of about 1:1000 is added to the chilling bath through which poultry are passed for a period of approximately 5 minutes following evisceration. Results indicate that the extract lengthens the shelf-life by more than 24 hours at 22°/24° C.

When the extract, in dilutions of 240, 360, 420 and 720 ppm, is used to treat fish meal contaminated with salmonella (20,000 cfu/g) tests of the cultures after 3 and 6 days show no growth of salmonella.

Three batches of feed (artificially contaminated fish meal, naturally contaminated fish meal, and naturally contaminated feather meal) contaminated with salmonella were treated with the extract of Example 1 at dilutions of 180, 300, 600, and 900 ppm. The salmonella cultures are tested after 3 and 5 days. The results will show that salmonella may survive in batches treated with 300 ppm or less, however, no growth will be detected at 600 and 900 ppm.

Rinsing of fish and seafood prior to packaging and/or freezing for approximately 3 minutes at dilutions of 200 ppm reduces bacteria contamination to less than 300 cfu/gram and is highly effective in killing faecal coliform *E. coli* and *staphylococcus aureus*.

EXAMPLE 6

The extract of Example 1 was used in a test to determine the inhibitory effects of a 200 ppm solution for *salmonella typhimurium* and *Escherichia coli* under defining conditions. Under this procedure, the extract was diluted to a concentration of 200 ppm with sterile deionized water and 10 ml aliquots dispensed aseptically into sterile screw-cap test tubes. 0.1 ml of an 18 hour TSB culture of the test organisms was added to the test solution and to a sterile water control. Each tube was briefly vortexed to insure mixing and held at 35° C. 1.0 ml aliquots were removed at 1, 3, 5 10, 15 and 30 minute intervals and viable organisms determined by standard plate count methods (incubation for 48 hours at 35° C. using standard methods agar).

While both tests began with an organism count of $9.8 \times 10^6$ after 1 minute and at all the other intervals, the organism count had been reduced to less than $10^3$.

While various examples have been described in detail hereinabove, it is apparent the invention is not limited to the specific details described, but departures may be made from such details without departing from the scope of the invention which is set forth in the accompanying claims:

What is claimed is:

1. A mouth rinse for use in the treatment of HIV infections, comprising approximately 50 ppm to about 100 ppm of a composition comprising ascorbic acid in an amount of approximately 16.5% and bioflavonoids in an amount in the range of 14–15%, said composition being extracted from a ground mixture of 80:20 dried grapefruit seeds:grapefruit pulp by weight, said extraction being carried out using a glycerin solution equal in weight to the weight of the ground mixture and at a temperature of approximately 150° C.

2. The mouth rinse according to claim 1 having the following approximate properties:

| pH | 2.5–3.0 |
| Specific gravity | 1.110 at 25° C. |
| Density | 9.37 |
| Viscosity Index | −23.2 |

3. The mouth rinse according to claim 1, wherein said grapefruits are selected from the group comprising Albeno, Ducan, March, Thompson, Ruby Red and Shaddon.

4. A mouth rinse for the treatment of HIV infections, comprising approximately 50 ppm to about 100 ppm of the reaction product obtained by contacting ground dried seeds and pulp of grapefruit with an equal amount by weight of glycerin to form said reaction product and separating the reaction product from the residue.

5. A method for the treatment of HIV infections, comprising the step of having a person with an HIV infection orally rinse and swallow with an effective amount of a reaction product comprising the product obtained by contacting a ground mixture of grapefruit seeds and pulp with an equal amount by weight of glycerin to form a reaction product and separating this product from the seed/pulp residue.

6. The method of claim 5 wherein the ratio of grapefruit seed to pulp is 80:20 by weight.

7. The method according to claim 5, wherein said reaction product is diluted to approximately 50–100 ppm.

8. A method for producing a composition for use in the treatment of HIV infections, the composition including approximately 16.5% ascorbic acid and 14–15% bioflavonoids from the seeds and pulp of grapefruit, comprising the steps of:

a. separating the seed and pulp of tree-ripened grapefruit;

b. drying the seed and pulp for 24–48 hours at a temperature in the range of 150°–200° C.;

c. mixing the dried seed and pulp at a ratio of 80:20 seed/pulp by weight;

d. grinding said seed/pulp mixture in a hammermill to small particles;

e. testing said mixture for the presence of pesticides and removing all pesticide contaminated particles from said mixture;

f. placing a glycerin solution in an extraction chamber;

g. heating said glycerin solution to a temperature of at least approximately 150° C.;

h. fixing a mesh container inside said extraction chamber, said mesh container including an amount of seed/pulp mixture equal in weight to said glycerin solution;

i. circulating said glycerin solution through said extraction chamber and through an external ultraviolet system and magnetic system to stabilize said reaction product and remove ferromagnetic constituents therefrom;

j. continuing step (i) at 150° C. for 3–4 hours;

k. reducing the temperature of said solution to approximately 60° C. and increasing the hydraulic pressure in said chamber to a range of 2500–3000 lbs.;

l. separating the resulting syrup from the residue;

m. passing the syrup through a force filter system having a 300–350 mesh nylon filter to obtain a heavy viscous lemon yellow liquid having a pH in the range of 2.5–3.0;

n. diluting the lemon yellow liquid between approximately 50 ppm to about 100 ppm for oral administration to a person with an HIV infection.

\* \* \* \* \*